United States Patent

Ikezaki et al.

[11] 4,054,659
[45] Oct. 18, 1977

[54] 5,7 DIHYDROXY-1-(TRIMETHOXYBENZYL)-1,2,3,H-TETRAHYDROISOQUINOLINES AND USE THEREOF

[75] Inventors: Muneyoshi Ikezaki, Ageo; Kunihiko Irie; Norihide Umino, both of Omiya; Katsuo Ikezawa, Urawa; Masanori Sato, Kuki, all of Japan

[73] Assignee: Tanabe Seiyaku Co., Ltd., Osaka, Japan

[21] Appl. No.: 627,259

[22] Filed: Oct. 30, 1975

[30] Foreign Application Priority Data
Nov. 20, 1974 Japan ............... 49-134734

[51] Int. Cl.² .............. A61K 31/47; C07D 213/65
[52] U.S. Cl. .............. 424/258; 260/289 D
[58] Field of Search ............. 260/289 D; 424/258

[56] References Cited

U.S. PATENT DOCUMENTS 3,873,704  3/1975  Yamato et al. ............ 424/258
3,978,063  3/1977  Kishimoto et al. ......... 424/258

FOREIGN PATENT DOCUMENTS 47-44,227  10/1972  Japan .................... 424/258

OTHER PUBLICATIONS

Shamma "The Isoquinoline Alkaloids, Chem. and Pharmacology", pp. 79 & 212, Academic Press (1972).

Primary Examiner—Donald G. Daus
Assistant Examiner—D. B. Springer
Attorney, Agent, or Firm—Bierman & Bierman

[57] ABSTRACT

A novel 5,7-dihydroxytetrahydroisoquinoline derivative having the formula:

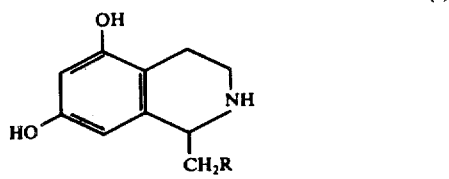

wherein R is trimethoxyphenyl, is prepared either by hydrolysis of a compound having the formula:

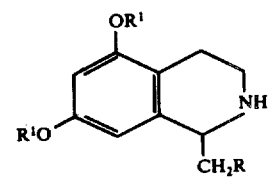

wherein $R^1$ is an organic acyl group and R is same as above, or by catalytic hydrogenation of a compound having the formula:

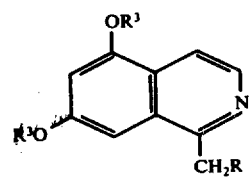

wherein $R^3$ is hydrogen or benzyl and R is same as above. The 5,7-dihydroxytetrahydroisoquinoline derivative (I) or a pharmaceutically acceptable acid addition salt thereof is useful as a bronchodilator.

4 Claims, No Drawings

5,7-DIHYDROXY-1-(TRIMETHOXYBENZYL)-1,2,3,H-TETRAHYDROISOQUINOLINES AND USE THEREOF

This invention relates to a novel 5,7-dihydroxy-tetrahydroisoquinoline derivative and a process for preparing the same. More particularly, it relates to a compound of the formula:

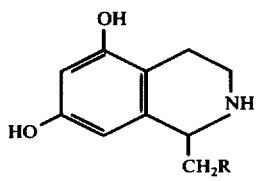

(I)

wherein R is trimethoxyphenyl, and a pharmaceutically acceptable acid addition salt thereof.

It is known that 6,7-dihydroxy-1-(3,4,5-trimethoxybenzyl)-1,2,3,4-tetrahydroisoquinoline is useful as a bronchodilator (U.S. Pat. No. 3,497,516). Said tetrahydroisoquinoline may be prepared by condensation of 6,7-dihydroxyphenethylamine with sodium 3-(3,4,5-trimthoxyphenyl)-glycidate or 3,4,5-trimethoxyphenylacetaldehyde. However, this condensation method can not be used for the synthesis of a tetrahydroisoquinoline having two hydroxy groups at the 5th and 7th-positions thereof because of the insufficient reactivity of 5,7-dihydroxy-phenethylamine. The present invention provides a novel 5,7-dihydroxy-tetrahydroisoquinoline. It also provides a novel method of preparing a 5,7-dihydroxy-tetrahydroisoquinoline.

The 5,7-dihydroxy-tetrahydroisoquinoline derivative (I) of the present invention or a pharmaceutically acceptable acid addition salt thereof has potent bronchodilating activity and is useful as a bronchodilator. Moreover, as compared with 6,7-dihydroxy-1-(3,4,5-trimethoxybenzyl)-1,2,3,4-tetrahydroisoquinoline, the 5,7-dihydroxy-tetrahydroisoquinoline derivative (I) of the present invention is more useful because of the longer duration of its point bronchodilating activity and/or lesser side effects (e.g., lesser increase of the heart rate). For example, when the bronchodilating activity of 5,7-dihydroxy-1-(3,4,5-trimethoxybenzyl)-1,2,3,4-tetrahydroisoquinoline (hydrochloride) of the invention is estimated by the preventive effects against serotonin-creatinin sulfate-induced bronchoconstriction after the duodenal administration thereof, said 5,7-dihydroxytetrahydroisoquinoline shows almost the same maximum preventive effects as that of 6,7-dihydroxy-1-(3,4,5-trimethoxybenzyl)-1,2,3,4-tetrahydroisoquinoline (hydrochloride). However, the bronchodilating activity of the former lasts for more than 3.5 hours at its maximum level, whereas the latter decreases to about 1/3 the maximum level after 3.5 hours.

The toxicity of the 5,7-dihydroxytetrahydroisoquinoline derivative (I) of the present invention is considerably low. For example, the 50% lethal dose ($LD_{50}$) of 5,7-dihydroxy-1-(3,4,5-trimethoxybenzyl)-1,2,3,4-tetrahydroisoquinoline (hydrochloride) which is estimated by intravenous injection thereof to mice is about 51 mg/kg.

The 5,7-dihydroxytetrahydroisoquinoline derivative (I) of the present invention can be used for pharmaceutical use either as the free base or a salt thereof. Pharmaceutically acceptable acid addition salts of the 5,7-dihydroxytetrahydroisoquinoline derivative (I) include, for example, hydrochloride, hydrobromide, perchlorate, nitrate, sulfate, phosphate, acetate, propionate, glycollate, lactate, ascorbate, maleate, fumarate, malonate, succinate, aspartate glutamate and nicotinate. The 5,7-dihydroxytetrahydroisoquinoline derivative (I) may be usedin the form of a pharmaceutical preparation for enteral or parenteral administration. The daily dose of the 5,7-dihydroxytetrahydroisoquinoline derivative (I) suitable for pharmaceutical use may be within the range of 10 to 500 μg/kg. Moreover, the 5,7-dihydroxytetrahydroisoquinoline derivative (I) may be used in conjunction or admixture with a pharmaceutical excipient which is suitable for enteral or parenteral administration. The excipient selected should be the one which does not react with the 5,7-dihydroxytetrahydroisoquinoline derivative (I). Suitable excipients include, for example, gelatin, lactose, glucose, sodium chloride, starch, magnesium stearate, talcum, vegetable oil and benzylalcohol. The pharmaceutical preparation may be a solid dosage form such as a tablet, a coated tablet, a pill, a troche, a capsule or pulveres; or in a liquid dosage form such as a solution, a suspension or an emulsion. The pharmaceutical preparation may further contain auxiliaries such as binders, diluents, stabilizing agents or emulsifying agents.

According to the present invention, the 5,7-dihydroxytetrahydroisoquinoline derivative (I) can be prepared by the steps of subjecting a 5,7-dibenzyloxy-1-trimethoxybenzylisoquinoline (II) to partial catalytic hydrogenation to give a 5,7-dihydroxy-1-trimethoxybenzylisoquinoline (III), reacting said isoquinoline (III) with an organic acylating agent, subjecting the resultant 5,7-diacyloxy-1-trimethoxybenzylisoquinoline (IV) to catalytic hydrogenation to give 5,7-diacyloxy-1-trimethoxybenzyl-1,2,3,4-tetrahydroisoquinoline (V), and then hydrolyzing the tetrahydroisoquinoline (V). Alternatively, the 5,7-dihydroxytetrahydroisoquinoline derivative (I) may be prepared by catalytic hydrogenation of the 5,7-dibenzyloxy-1-trimethoxybenzylisoquinoline (II) or the 5,7-dihydroxy-1-trimethoxybenzylisoquinoline (III). The above-mentioned reactions of the present invention are shown by the following scheme:

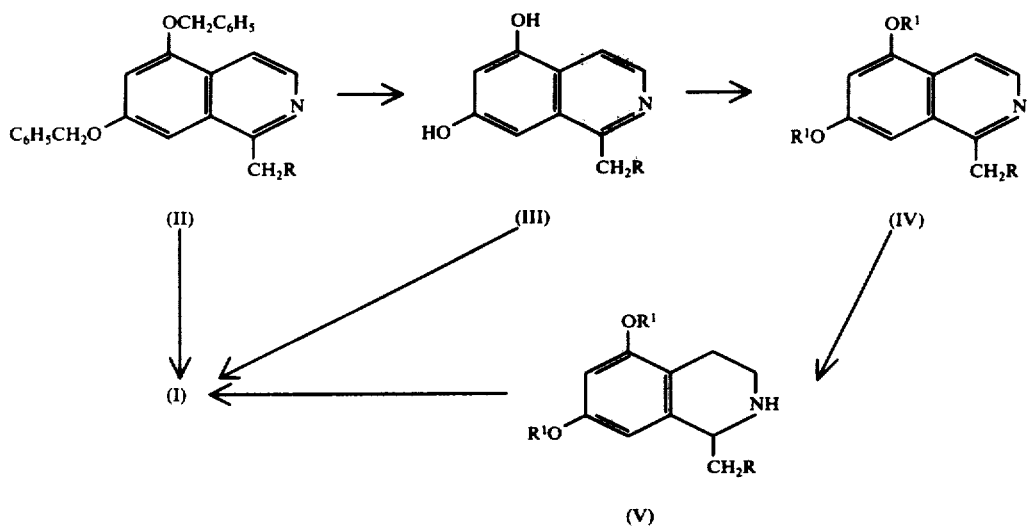

(V)

wherein R¹ is an organic acyl group and R is the same as defined above.

The partial catalytic hydrogenation of 5,7-dibenzyloxy-1-trimethoxybenzylisoquinoline (II) can be conducted by shaking the isoquinoline (II) in the presence of a catalyst in a hydrogen atmosphere. It is preferred to carry out the reaction at a temperature of 5° to 40° under atmospheric pressure A lower alkanol (e.g., methanol, ethanol, propanol) or a mixture of the lower alkanol and water is suitable as the reaction solvent. Preferred examples of the catalyst include palladium, palladium-carbon, Raney-nickel and cobaltous dioxide. When platinum or platinum dioxide is employed as the catalyst in this hydrogenation reaction, a mixture of the 5,7-dihydroxytetrahydroisoquinoline derivative (I) and the 5,7-dihydroxy-1-trimethoxybenzylisoquinoline (III) may be obtained as the reaction product.

The subsequent reaction of the isoquinoline (III) with the organic acylating agent is accomplished in a conventional manner. For example, said reaction can be carried out in the presence or absence of an acid acceptor. Suitable examples of the acid acceptor include organic tertiary amines (e.g., pyridine, triethylamine), alkali metal hydroxide (e.g., sodium hydroxide) and alkali metal carbonates (e.g., sodium carbonate). The reactive derivatives (e.g., acid halide, acid anhydride) of a fatty acid having one to 5 carbon atoms (e.g., acetic acid, propionic acid, butyric acid) and benzoic acid are suitably employed as the organic acylating agent. It is preferred to carry out the reaction at a temperature of 0° to 40° C. When pyridine is used as the acid acceptor, said reaction may be preferably carried out by dissolving the isoquinoline (III) to pyridine and then adding the organic acylating agent thereto under cooling. Further, when acetic anhydride is employed as the acylating agent, the 5,7-diacyloxy-1-trimethoxybenzylisoquinoline (IV) is prepared by heating said anhydride and the isoquinoline (III).

The catalytic hydrogenation of the 5,7-diacyloxy-1-trimethoxybenzylisoquinoline (IV) can be carried out in the presence of platinum or platinum dioxide in a hydrogen atmosphere. It is preferred to carry out the reaction at a temperature of 5° to 40° C under a pressure of one to two atmospheres, especially under an acidic condition (e.g., pH 6 to 4). A lower alkanol (e.g., methanol, ethanol, propanol) or a mixture of the lower alkanol and water is suitable as the reaction solvent.

The 5,7-dihydroxytetrahydroisoquinoline derivative (I) is prepared by acidic or alkaline hydrolysis of the resultant 5,7-diacyloxy-1-trimethoxybenzyl-1,2,3,4-tetrahydroisoquinoline (V). Said acidic or alkaline hydrolysis can be carried out by a conventional manner, for example, by treating the isoquinoline (V) with a mineral acid (e.g., hydrochloric acid, hydrobromic acid, sulfuric acid), an alkali metal hydroxide (e.g., sodium hydroxide, potassium hydroxide) or an alkali metal bicarbonate (e.g., sodium bicarbonate). It is preferred to carry out the hydrolysis at a temperature of 10° to 60° C in a solvent. Water a lower alkanol (e.g., methanol, ethanol) or a mixture thereof is suitable as the reaction solvent. The 5,7-dihydroxytetrahydroisoquinoline derivatie (I) is also prepared by catalytic hydrogenation of the 5,7-dihydroxy-1-trimethoxybenzylisoquinoline (III). Said catalytic hydrogenation may be conducted under the same conditions as employed in the hydrogenation reaction of the 5,7-diacyloxy-1-trimethoxybenzylisoquinoline (IV).

The starting compound of the present invention, i.e., the 5,7-dibenzyloxy-1-trimethoxybenzylisoquinoline (II), is a novel compound. This novel starting compound (II) is prepared by the steps of subjecting 1-[N-(3,5-dibenzyloxybenzyl)-N-p-tosyl-amino]-2,2-diethoxyethane (VI) to Pomeranz-Fritsch's intramolecular cyclization to give 5,7-dibenzyloxyisoquinoline (VII), reacting said 5,7-dibenzyloxyisoquinoline with an organic acylating agent and cyanogen hydride or an alkali metal salt thereof to give a 2-acyl-1-cyano-5,7-dibenzyloxy-1,2-dihydroisoquinoline (VIII), condensing an alkali metal salt of the dihydroisoquinoline (VIII) with a trimethoxybenzyl halide, and then hydrolyzing the resultant 2-acyl-1-cyano-5,7-dibenzyloxy-1-trimethoxybenzylisoquinoline (IX). These reactions are shown by the following scheme:

(VI)

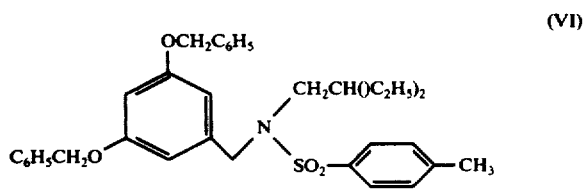

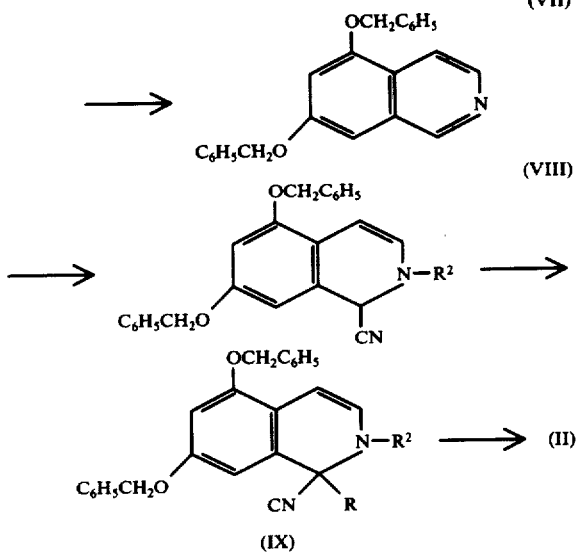

wherein R² is an organic acyl group and R is the same as defined above.

1-[N-(3,5-dibenzyloxybenzyl)-N-p-tosyl-amino]-2,2-diethoxyethane (VI) is readily obtainable. For example, said compound (VI) is prepared by condensing 3,5-dibenzyloxybenzaldehyde with 1-amino-2,2-diethoxyethane at 60° to 100° C, reducing the resultant 1-[N-(3,5-dibenzyloxybenzylidene)amino]-2,2-diethoxyethane with sodium borohydride in ethanol under refluxing to give 1-[N-(3,5-dibenzyloxybenzyl)amino]-2,2-diethoxyethane, and then reacting said product with p-tosyl chloride in pyridine under ice-cooling.

The Pomeranz-Fritsch's intramolecular cyclization is preferably conducted by treating the compound (VI) with an acid at a temperature of 80° to 110° in a solvent (e.g., dioxane). Preferred examples of said acid include hydrochloric acid, sulfuric acid, phosphoric acid and p-toluenesulfonic acid.

The reaction of the 5,7-dibenzyloxyisoquinoline (VII) with the organic acylating agent and cyanogen hydride or an alkali metal salt thereof is carried out at a temperature of −5° to 20° C in a solvent (e,g., water, dichlormethane). The reactive derivative of an acid (e.g., benzoyl halide) is suitably employed as the acylating agent. When potassium cyanide is employed as the alkali metal salt of cyanogen hydride, this reaction is preferably carried out by dissolving the compound (VII) in methylene chloride, adding thereto an aqueous potassium cyanide solution, and then adding benzoyl chloride to the mixture at a temperature lower than 0° C.

The alkali metal salt of the dihydroisoquinoline (VIII) may be prepared by treating the dihydroIsoquinoline (VII) with an alkali metal (e.g., lithium, sodium, potassium), an alkali metal hydride (e.g., sodium hydride, lithium hydride) or an alkali metal amide (e.g., sodium amide, potassium amide, lithium amide, lithium diisopropylamide), preferably under ahydrous conditions. The condensation reaction of a trimethoxybenzyl halide with the alkali metal salt of the dihydroisoquinoline (VIII) is carried out at a temperature lower than 0° C, especially lower than −10° C, in a solvent (e.g., dimethylformamide). The condensation product thus obtained, i.e., the 2-acyl-1-cyano-5,7-dibenzyloxy-1-trimethoxybenzylisoquinoline (IX), is then hydrolyzed to give the 5,7-dibenzyloxy-1-trimethoxybenzylisoquinoline (II).

Said hydrolysis can be readily carried out by treating the trimethoxybenzylisoquinoline (IX) with an alkali agent (e.g., alkali metal hydroxide, alkali metal carbonate) at a temperature of 30° to 80° C in a solvent (e.g., dioxane).

Practical and presently-preferred embodiments of the present invention are illustratively shown in the following Examples:

EXAMPLE 1

1. 4.6 g of 3,5-dibenzyloxybenzaldehyde are added to 3.0 g of 1-amino-2,2-diethoxyethane, and the mixture is heated at 100° C for 10 minutes. Then, the mixture is stirred at 60° C for 2.5 hours under reduced pressure until water is removed from the mixture. 6.3 g of 1-[N-(3,5-dibenzyloxybenzylidene)amino]-2,2-diethoxyethane is thereby obtained as an oil. 5.9 g of this product are dissolved in 100 ml of ethanol. 600 mg of sodium borohydride are added to the ethanol solution, and the mixture is refluxed for 2 hours. After the reaction, water is added to the mixture and the aqueous mixture is extracted with ethyl acetate. The extract is dried and then evaporated to remove solvent, whereby 5.9 g of 1-[N-(3,5-dibenzyloxybenzyl)amino]-2,2-diethoxyethane are obtained.

Infrared absorption spectrum:
$\nu_{max.}^{liquid}$: 3330, 1600, 1595, 1150, 1060 cm$^{-1}$ 12.7 g of 1-[N-(3,5-dibenzyloxybenzylamino]-2,2-diethoxyethane are dissolved in 60 ml of pyridine, and 5.6 g of p-tosyl chloride are added thereto under ice-cooling. The solution is allowed to stand at the same temperature for 4 hours. Then, the reaction solution is poured into ice-10% hydrochloric acid, and extracted with ethyl acetate. The extract is washed with water, dried and then evaporated to remove solvent. 12.6 g of 1-[N-(3,5-dibenzyloxybenzyl)-N-p-tosyl-amino]-2,2-diethoxyethane are thereby obtained as an oil Mass analysis: m/e 589 (M+)

2. 8 ml of 10% hydrochloric acid are added to 46 ml of a dioxane solution containing 12.6 g of 1-[N-(3,5-dibenzyloxybenzyl)-N-p-tosyl-amino]-2,2-diethoxyethane. The mixture is stirred at 90° C for 24 hours. Then, the mixture is poured into ice-water. The aqueous mixture is alkalified with potassium carbonate and extracted with etyl acetate. The extract is washed with water, dried and then evaporated to remove solvent. The crude product thus obtained is recrystallized from ethanol. 3.3 g óf 5.7-dibenzyloxyisoquinoline are thereby obtained as colorless crystals. Yield: 48.5% M.p. 113° − 115° C.

3. A solution of 3 g of potassium cyanide in 15 ml of water is added to 25 ml of a methylene chloride solution containing 3.3 g of 5,7-dibenzyloxyisoquinoline. 6.4 g of benzoyl chloride are added to the mixture at 0° C for 2 hours under stirring. After the mixture is allowed to stand at room temperature, the methylene chloride layer is separated therefrom. The methylene chloride solution separated is washed with an aqueous 1% sodium hydroxide solution and water, respectively. The methylene chloride solution is then dried and evaporated to remove solvent. The oily residue thus obtained is dissolved in 10 ml of ether, and this solution is poured onto a silica gel column. The column is eluted with a mixture of ether and hexane. The eluate is evaporated to remove solvent, and the crystalline residue thus obtained is recrystallized from ethanol. 4 g of 2-benzoyl-1- cyano-5,7-dibenzyloxy-1,2-dihydroisoquinoline are thereby obtained. Yield: 64% M.p. 123° - 125° C.

4. Sodium hydride (prepared by washing 553 mg of 65% sodium hydride with absolute n-hexane) is suspended in 15 ml of dimethylformamide. A solution of 3.4 g of 2-benzoyl-1-cyano-5,7-dibenzyloxy-1,2-dihydroisoquinoline in 40 ml of dimethylformamide is added dropwise to the suspension at −10° C in a nitrogen atmosphere. Then, a solution of 1.71 g of 3,4,5-trimethoxybenzyl chloride in 40 ml of dimethylformamide is added dropwise to the mixture for 30 minutes, and the mixture is allowed to stand at the same temperature for 30 minutes. The reaction mixture is poured into ice-water, and extracted with ethyl acetate. The extract is evaporated to remove solvent, whereby 2-benzoyl-1-cyano-5,7-dibenzyloxy-1-(3,4,5-trimethoxybenzyl)-1,2-dihydroisoquinoline is obtained as a crude oil. The crude oil is dissolved in 200 ml of dioxane. 50 ml of an aqueous 10% sodium hydroxide solution are added to the dioxane solution, and this mixture is stirred at 50° C for 12 hours. After the reaction, the mixture is evaporated under reduced pressure to remove solvent. The residue thus obtained is extracted with methylene chloride. The methylene chloride extract is washed with water, dried and then evaporated to remove solvent. 3.1 g of 5,7-dibenzyloxy-1-(3,4,5-trimethoxybenzyl)-isoquinoline are obtained as a crude product. Yield: 84% M.p. 158° - 160° C (recrystallized from ethanol).

5. 0.2 g of 5.7-dibenzyloxy-1-(3,4,5-trimethoxybenzyl)-isoquinoline is dissolved in 250 ml of ethanol, and 0.05 g ot 10% palladium-carbon is added thereto. The mixture is shaken at 25° C in a hydrogen atmosphere. After the hydrogen uptake is completed, the catalyst is removed by filtration. The filtrate is evaporated to remove solvent. 0.125 g of 5,7-dihydroxy-1-(3,4,5-trimethoxybenzyl)-isoquinoline is thereby obtained as a crude product. Yield: 95% M.p. 270° - 275° C (decomp.) (recrystallized from ethanol).

6. 0.8 g of 5,7-dihydroxy-1-(3,4,5-trimethoxygbenzyl)-isoquinoline is dissolved in 30 ml of pyridine, and 0.955 g of acetic anhydride is added thereto under cooling. The mixture is allowed to stand at room temperature for 4 hours. The reaction mixture is poured into water and extracted with ethyl acetate. The extract is washed with water, dried and then evaporated to remove solvent. 0.9 g of 5,7-diacetoxy-1-(3,4,5-trimethoxybenzyl)-isoquinoline is thereby obtained as a crude product. Yield: 90.5% M.p. 118° - 120° C (recrystallized from ethanol).

7. 0.78 g of 5,7-diacetoxy-1-(3,4,5-trimethoxybenzyl)-isoquinoline hydrochloride is dissolved in 200 ml of ethanol, and 0.3 g of platinum dioxide is added thereto. The mixture is shaken at 25° C in a hydrogen atmosphere. After the hydrogen uptake is completed, the catalyst is removed by filtration. 50 ml of a hydrochloric acid-ethanol solution (the content of hydrochloric acid: 9%) are added to the filtrate, and this mixture is heated at 50° C for 5 minutes. Then, the mixture is evaporated to remove solvent, and the residue thus obtained is recrystallized from a mixture of ethanol and isopropyl ether. 0.6 g of 5,7-dihydroxy-1-(3,4,5-trimethoxybenzyl)-1,2,3,4-tetrahydroisoquinoline hydrochloride is thereby obtained. Yield: 94.6% M.p. 240° - 243° C.

EXAMPLE 2

A mixture of 1.4 g of 5,7-dibenzyloxy-1-(3,4,5-trimethoxybenzyl)-isoquinoline, 0.7 g of platinum dioxide, 100 ml of a hydrochloric acid-ethanol solution (the content of hydrochloric acid: 9%) and 50 ml of ethanol is shaken at 25° C in hydrogen atmosphere. After 150 ml of hydrogen are absorbed, the catalyst is removed by filtration. The filtrate is evaporated to remove solvent, whereby a mixture of 5,7-dihydroxy-1-(3,4,5-trimethoxybenzyl)-isoquinoline hydrochloride and 5,7-dihydroxy-1-(3,4,5-trimethoxybenzyl)-1,2,3,4-tetrahydroisoquinoline hydrochloride is obtained. This mixture is recrystallized 33 times from ethanol, whereby 0.3 g of 5,7-dihydroxy-1-(3,4,5-trimethoxybenzyl)-1,2,3,4-tetrahydrolsoquinoline hydrochloride is obtained. Yield: 40% The physiocochemical properties of this product are identical with those of the compound obtained in Example 1.

EXPERIMENTS

Bronchodilating activity

Cats were anesthetized with sodium pentobarbital (40 mg/.kg, i.p.). Under artificial respiration (13 - 15 ml of air/kg/stroke, 30 strokes/minute) thereof, the cats were immobilized by intraveous injection of gallamine triethyodide (8 mg/kg). Serotonin.creatinin sulfate (=bronchoconstrictor) was injected intravenously to the cats at the dose of 20 μg/kg, and the intratracheal pressure was measured by means of a pressure transducer. Then, each one of test compounds was administered to the duodenum of the cats at the dose of 10 μg/kg, and the intratracheal pressure and the heart rate were measured with the passage of time. The bronchodilating activity was estimated by the preventive effects (%) of each test compound against bronchoconstriction. The results are shown in the following Table.

| Period of time after the administration (minutes) | Preventive effects against bronchoconstriction (%) | | Increase of heart rate (Number of heart beats increased/minute) | |
|---|---|---|---|---|
| | Compound A* | Compound B** | Compound A* | Compound B** |
| 5 | 8.5 ± 3.2 | 21.1 ± 8.6 | 1.3 ± 0.3 | 9.4 ± 3.1 |
| 15 | 47.9 ± 8.5 | 71.2 ± 7.6 | 10.6 ± 3.4 | 35.4 ± 8.3 |
| 30 | 63.5 ± 9.9 | 77.6 ± 5.2 | 22.2 ± 6.5 | 35.6 ± 7.7 |
| 45 | 69.7 ± 8.7 | 73.9 ± 2.6 | 21.3 ± 5.2 | 27.2 ± 4.8 |
| 60 | 71.1 ± 7.1 | 67.2 ± 3.4 | 20.0 ± 4.4 | 20.4 ± 4.0 |
| 75 | 70.7 ± 6.8 | 62.3 ± 5.1 | 18.7 ± 3.8 | 16.8 ± 3.7 |
| 90 | 72.5 ± 6.1 | 54.7 ± 6.0 | 17.8 ± 3.0 | 13.6 ± 3.6 |
| 120 | 71.0 ± 5.6 | 45.5 ± 7.5 | 17.2 ± 2.3 | 10.2 ± 3.7 |
| 150 | 70.2 ± 6.4 | 38.0 ± 8.7 | 15.2 ± 2.1 | 8.0 ± 3.8 |
| 180 | 69.1 ± 5.7 | 31.6 ± 9.5 | 13.7 ± 1.4 | 6.8 ± 3.6 |
| 210 | 64.6 ± 7.4 | 26.0 ± 7.4 | 12.0 ± 1.4 | 5.6 ± 3.4 |

Note:
*5,7-dihydroxy-1-(3,4,5-trimethoxybenzyl)-1,2,3,4-tetrahydroisoquinoline hydrochloride (the compound of the present invention)
**-6,7-dihydroxy-1-(3,4,5-trimethoxybenzyl)-1,2,3,4-tetrahydroisoquinoline hydrochloride (the compound disclosed in U.S. Pat. No. 3497516)

What we claim is:

1. A compound of the formula:

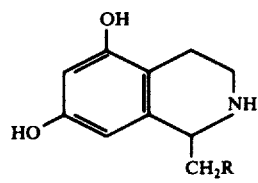

wherein R is trimethoxyphenyl, or a pharmaceutically acceptable acid addition salt thereof.

2. The compound of claim 1, in which R is 3,4,5-trimethoxyphenyl.

3. A pharmaceutical composition consisting essentially of a bronchodilating effective amount of the compound of claim 1 and a pharmaceutically acceptable carrier.

4. A pharmaceutical composition consisting essentially of a bronchodilating effective amount of the compound of claim 2 and a pharmaceutically acceptable carrier.